United States Patent [19]

Baer

[11] Patent Number: 5,419,776
[45] Date of Patent: May 30, 1995

[54] PNEUMOTHORAX TREATMENT DEVICE

[76] Inventor: Robert M. Baer, 502 NW. 72nd Terr.,, Kansas City, Mo. 64118

[21] Appl. No.: 129,445

[22] Filed: Sep. 30, 1993

[51] Int. Cl.⁶ .............................................. A61M 5/00
[52] U.S. Cl. .................................. 604/246; 604/247; 604/264; 604/35; 604/283
[58] Field of Search ............... 604/247, 222, 411, 414, 604/264, 266, 272, 177, 246, 245, 280, 32, 30, 280, 283, 905; 137/854, 858, 68.1, 614.21

[56] References Cited

U.S. PATENT DOCUMENTS

| | | | |
|---|---|---|---|
| 2,867,213 | 1/1959 | Thomas | 604/247 |
| 3,758,073 | 9/1973 | Schutle . | |
| 4,141,379 | 2/1979 | Manske | 604/246 |
| 4,153,058 | 5/1979 | Nehme . | |
| 4,232,677 | 11/1980 | Leibinsohn . | |
| 4,342,315 | 8/1982 | Jackson | 604/35 |
| 4,387,879 | 6/1983 | Tauschinski . | |
| 4,465,062 | 8/1984 | Versaggi et al. . | |
| 4,556,086 | 12/1985 | Raines . | |
| 4,566,493 | 1/1986 | Edwards et al. . | |
| 4,573,965 | 3/1986 | Russo . | |
| 4,683,916 | 8/1987 | Raines . | |
| 4,781,675 | 11/1988 | White | 604/247 |
| 4,813,941 | 3/1989 | Shea . | |
| 5,071,411 | 12/1991 | Hillstead | 604/246 |
| 5,098,405 | 3/1992 | Peterson et al. | 604/246 |
| 5,203,771 | 4/1993 | Melker et al. | 604/86 |

OTHER PUBLICATIONS

Laerdal, 1993 Life Saving Products Catalog, p. 42.

Primary Examiner—C. Fred Rosenbaum
Assistant Examiner—Chalin Smith
Attorney, Agent, or Firm—Litman, McMahon & Brown

[57] ABSTRACT

An apparatus for treating pneumothorax and pneumohemothorax comprises a one-way valve having a top end and a bottom end and a suction port secured to and extending beyond the top end, a conduit secured to and extending perpendicularly away from the bottom end of the one-way valve in flow communication therewith a 90 degree elbow removably securable to a distal end of the conduit in flow communication therewith and a luer lock lug receptacle secured to the 90 degree elbow and adapted to threadingly receive luer lock lugs on a large bore needle or catheter. The 90 degree elbow is removably securable to the conduit and may be removed and replaced with a connection adapter. The connection adaptor has a first end removably securable to the distal end of the conduit and a second end removably securable to a chest tube surgically inserted in the pleural space. The apparatus may also include an injection port extending from and in flow communication with the conduit. The injection port being adapted to receive a needle such that an aqueous solution may be directed toward said one-way valve from said needle.

4 Claims, 1 Drawing Sheet

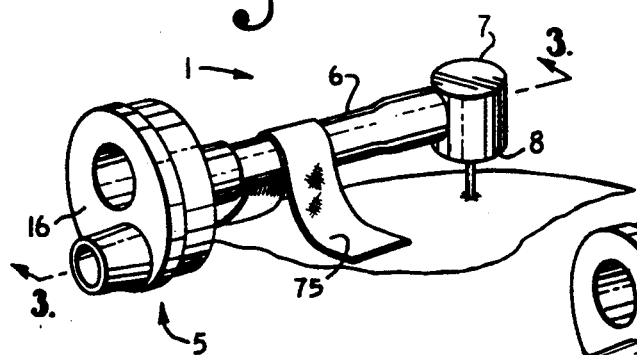
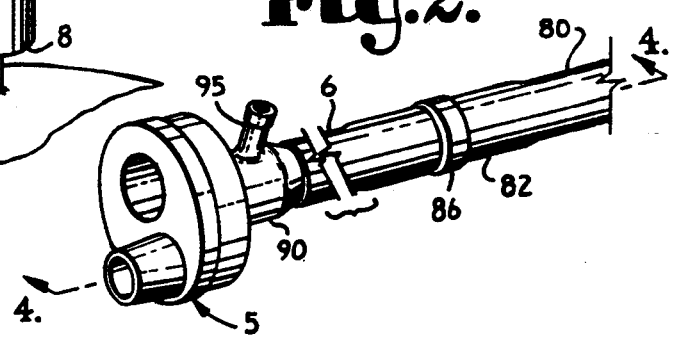
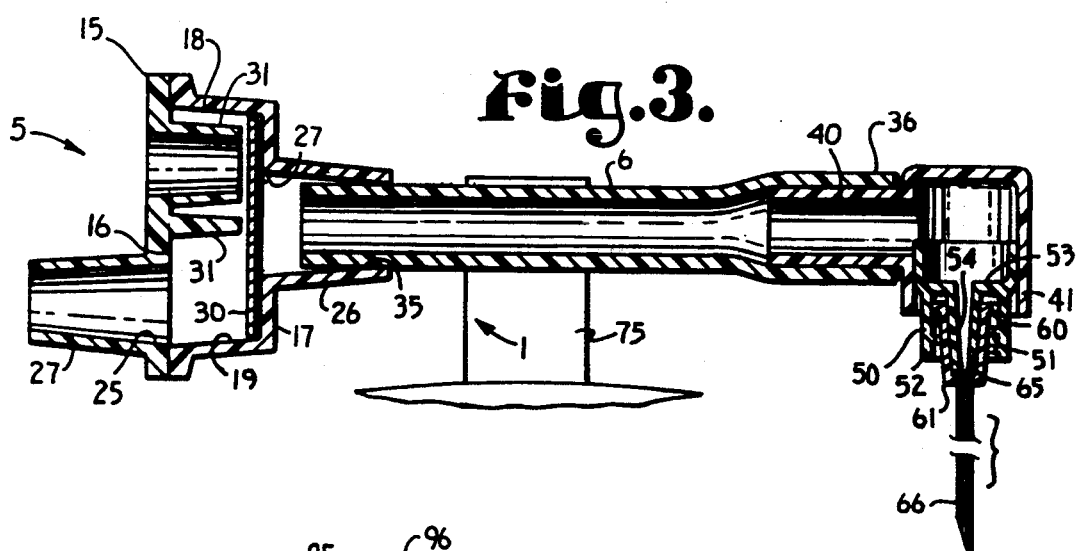
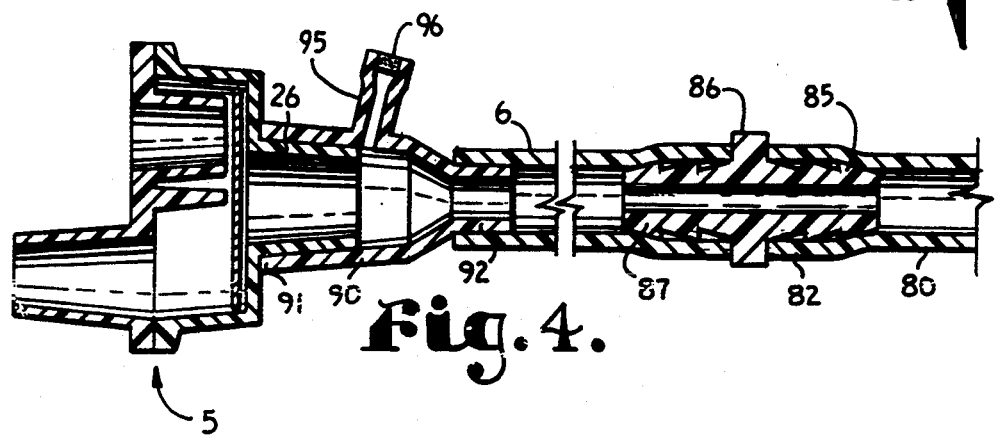

PNEUMOTHORAX TREATMENT DEVICE

BACKGROUND OF THE INVENTION

The present invention relates to a device for treating pneumothorax and pneumohemothorax. Pneumothorax is the accumulation of air or gas in the pleural space which houses the lungs. A pneumohemothorax is the accumulation of air and blood in the pleural space. Either may occur spontaneously as the result of trauma or through a pathological process.

The pleural space is the cavity in the thorax within which the lungs are retained. When we breathe in, our muscles cause the chest walls to move up and out and our diaphragm at the lower portion of the thorax to move down. The lungs, being exposed to greater atmospheric pressure through airways to the mouth or nose, expand with air to fill the increasing volume and equalize the pressure difference. When a person breathes out, the chest walls move down and in and the diaphragm moves up which squeezes the lungs and forces air from the lungs through the airways. The lungs, maintained in the pleural space expand in response to the partial vacuum created when the chest wall moves out and the diaphragm moves down. If the partial vacuum is released or broken, the forces maintaining the lungs in an expanded position are broken and the lung collapses.

Trauma to the chest area such as through a gun shot or knife wound allows air and fluid to enter the pleural space and breaks or releases the partial vacuum therein. The presence of air and fluid in the pleural space prevents expansion of the lung therein. In some cases, the wound acts as a one-way valve allowing air to be pulled into the pleural space as the chest cavity expands, but prevents air from escaping when the diaphragm raises and the chest cavity contracts. If the partial vacuum is not restored to the pleural cavities and the air and fluid therein removed, pneumothorax or pneumohemothorax can be fatal.

Treatment of pneumothorax or pneumohemothorax generally involves patching the wound and then removing the entrapped air or fluid from the pleural space. In hospitals, the air is removed by surgically inserting a tube into the pleural space through an incision between ribs. The tube is then connected to a vacuum source for evacuating the space or the tube is connected to a one-way valve which allows air or fluid to exit the pleural space, but prevents the air or fluid from re-entering as the chest cavity expands and contracts through normal breathing.

When treating pneumothorax or pneumohemothorax in the field, emergency medical technicians, paramedics or the like, typically do not have time to surgically insert a tube into the pleural space. Instead, the emergency care provider will insert a large bore needle or catheter into the pleural space. Prior to insertion of the needle or catheter, the emergency care provider will use the fingertip of a rubber glove to form a one-way valve on the end of the catheter. The finger-tip is cut from a glove and the needle or catheter inserted through the end thereof, such that the open end of the finger-tip extends past the end of the needle or catheter. When the chest cavity contracts during exhalation, air is forced through the needle or catheter and past the rubber glove fingertip. During inhalation as the chest cavity expands to create a partial vacuum, the partial vacuum cause the sides of the rubber glove fingertip to collapses preventing air from entering the pleural space.

The main drawbacks to the fingertip one-way valve arrangement are the time it takes to make the one-way valve, by cutting the fingertip and inserting the needle therethrough and the inability of the fingertip one-way valve to consistently form a good seal.

U.S. Pat. No. 4,813,941 discloses a pneumothorax treatment device comprising a one-way valve having a luer lock receiving adaptor secured thereto, such that the one-way valve can be quickly connected to standard needles and catheters incorporating luer lock lugs. In the field, the emergency care providers simply inserts the needle or catheter into the pleural space, then connects a pre-formed one-way valve thereto using the luer lock adaptor such that the one-way valve may be rapidly connected to the luer lock connecting lugs of standard catheters. Although an improvement over the rubber glove fingertip one-way valve, this device does have its limitations. In particular, the device is difficult to secure to a patient during transportation, the device is not adaptable to be hooked up to a suction device and the valve is prone to sticking due to blood and other fluids entering the valve body and drying.

SUMMARY OF THE INVENTION

The present invention generally comprises a one-way valve which is quickly and interchangeably securable to a chest tube or to a standard hypodermic needle or catheter incorporating luer lock lugs for use in removing air or fluid from the pleural space.

The apparatus comprises a one-way valve having a top end and a bottom end and a suction port extending beyond said top end, a conduit secured to and extending perpendicularly from the bottom end of the one-way valve, a 90 degree elbow secured to a distal end of the conduit, and a luer lock lug receptacle means secured to the 90 degree elbow and adapted to threadingly receive the luer lock lugs on a catheter or hypodermic needle. The 90 degree elbow is removably securable to the distal end of the conduit and may be replaced with a connection adapter having a first end removably securable to the distal end of the conduit and a second end removably securable to an end of a chest tube wherein an opposite end of the chest tube is surgically inserted into the pleural space.

The apparatus may also include an injection port extending from the conduit and adapted to receive a needle such that an aqueous solution may be directed toward the one-way valve from the needle. The injection port preferably includes sealing means for sealing the port upon removal of the needle therefrom.

OBJECTS AND ADVANTAGES OF THE INVENTION

Therefore, it is an object of this invention to provide an improved pneumothorax treatment device; to provide such a device comprising a one-way valve which is readily connectable in flow communication with standard catheters and needles; to provide such a device which is interchangeably connectable to a chest tube; to provide such a device which is readily connectable to a vacuum source; to provide such a device which is readily securable to a patient during transport; and to provide such a device which is relatively inexpensive to manufacture and particularly well adapted for its intended usage.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view of the pneumothorax treatment device of the present invention incorporating a catheter inserted in a patient.

FIG. 2 is a perspective view of an alternative embodiment of the present invention secured to a chest tube.

FIG. 3 is an enlarged and fragmentary cross-sectional view generally taken along line 3—3 of FIG. 1.

FIG. 4 is an enlarged and fragmentary cross-sectional view taken along line 4—4 of FIG. 3.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail the reference numeral 1 generally refers to a pneumothorax treatment device of the present invention. The pneumothorax treatment device 1 generally comprises a one-way valve 5, a connecting conduit 6, a 90 degree elbow 7 and a luer lock lug receptacle 8.

The one-way valve 5 may be of the type manufactured by Laerdal as the One Way Valve For Laerdal Pocket Mask Cat No. 820300. The valve 5 comprises a housing 15 having a top wall 16, a bottom wall 17, and a cylindrical side wall 18 which form a valve chamber 19. A suction port 24 extends away from an exhaust opening 25 in the top wall 16 and in flow communication with the valve chamber 19. An intake port 26 extends away from an intake opening 27 in the bottom wall 17 such that the intake port 26 is in flow communication with the valve chamber 19. A disk 30 is positioned in the valve chamber 19 so as to extend across the intake opening 27. Stops 31 project into the valve chamber 19 from the top wall 16 toward the bottom wall 17 and prevent the disk 30 from advancing into covering engagement with the exhaust opening 25.

The conduit 6 is preferably formed from non-collapsible suction type tubing. A first end 35 of the conduit 6 has an outer diameter slightly larger than the inner diameter of the intake port 26 of the one-way valve 5. The conduit 6 is secured to the intake port 26 by inserting the first end 35 of the conduit into the intake port 26 to form a friction fit. The conduit 6 is in flow communication with the one-way valve 5 when secured thereto.

A distal end or second end 36 of the conduit 6 is secured to the 90 degree elbow 7. The 90 degree elbow 7 is preferably formed from rigid plastic and includes a connection arm 40 and a receiving arm 41. The outer diameter of the connection arm 40 is slightly larger than the inner diameter of the conduit 6. The connection arm 40 is inserted into the conduit 6 and secured thereto by friction. The 90 degree elbow 7 is in flow communication with the conduit 6.

The luer lock lug receptacle 8 is secured within the receiving arm 41 of the 90 degree elbow 7 as shown in FIGS. 2 and 4 by gluing, sonic welding or the like. The luer lock lug receptacle 8 generally includes a cylindrical wall 50 having internal threads 51 extending from an open end 52 to a transverse wall 53 extending across the cylindrical wall 50. A coupling tube 54 extends through the transverse wall 53 and beyond the open end 52 of the luer lock lug receptacle 8.

The cylindrical wall 52 and the internal threads 51 are sized to receive and engage the lugs 60 on standard hypodermic needles or venous catheters 61. The needle or catheter 61 includes a coupling tube receptacle 65. The lugs 60 are secured at one end of the coupling tube receptacle 65 and a body invasive tubular portion or lumen 66 of the hypodermic needle or catheter 61 is secured at an opposite end of the coupling tube receptacle 65.

For treating pneumothorax or pneumohemothorax it is preferable to use a needle or catheter 61 having a lumen of relatively large internal diameter or gauge. When a needle or catheter 61 is threadingly secured to the receptacle 8, the coupling tube 54 of the luer lock lug receptacle 8 extends into the coupling tube receptacle 65 of the needle or catheter 61 such that the needle or catheter 61 is in flow communication with the luer lock lug receptacle 8, the 90 degree elbow 7, the conduit 6 and the one-way valve 5.

When an emergency medical practitioner treats a patient having a pneumothorax or pneumohemothorax, the practitioner initially patches any open wounds allowing air to enter the pleural space then inserts a standard needle or catheter 61 having luer lock lugs 60 thereon into the pleural space between two ribs. The pneumothorax treatment device 1 is then secured to the needle or catheter 61 by positioning the luer lock lug receptacle 8 on top of the lugs 60 and rotating the device 1 such that the internal threads 51 of the luer lock lug receptacle 8 engage the lugs 60.

As the patient exhales, air and fluid trapped in the pleural space is then forced out of the pleural space through the needle or catheter 61, the luer lock lug receptacle 8, the 90 degree elbow 7, the conduit 6 and the one way valve 5. The force of the escaping air and fluid forces the disk 30 against the stops 31 such that the air and fluid can then escape around the disk 30 and out of the exhaust opening 25. When the patient inhales, the slight vacuum created in the pleural space is communicated through the device 1 such that the disk 30 is pulled against the bottom wall 17 of the valve housing 15 so as to cover the intake opening 27 thereby preventing air from being drawn into the pleural space through the device 1. If a more rapid evacuation of air and fluid through the pleural space is desired, a suction tube may be connected to the suction port 24 of the valve 5 and the suction tube can be connected to vacuum means for pulling a slight vacuum through the device 1.

After attachment of the pneumothorax treatment device to a patient in the field, the patient is then transported to a hospital for further treatment. During transport of the patient, the device 1 needs to be secured in place. Securement of the device 1 is readily accomplished by securing the device 1 to the body of the patient using a length of tape 75. When the device 1 is attached to a needle or catheter 61 the conduit 6 generally extends in parallel alignment with the patients chest. The tape 75 is preferably laid perpendicularly across the conduit 6 and the ends are then pressed against the patient's skin for securement thereto.

When the patient arrives at the hospital, it is often preferable to insert a chest tube 80 into the pleural space to facilitate removal of air and fluid therefrom. A first end (not shown) of the chest tube 80, is surgically inserted into the pleural space. The pneumothorax treatment device 1 is adaptable to be secured to a second end 82 of the chest tube 80.

In particular and as generally shown in FIG. 4, the 90 degree elbow 7 is removed from the second end 36 of the conduit 6 and a first connector end 85 of a tube connector or connection adapter 86 is inserted therein. A second connector end 87 of the tube connector 86 is then inserted in the second end 82 of the chest tube 80. The tube connector 86 is hollow such that the conduit 6 flow communicates with the chest tube 80 when the two are connected by the tube connector 86.

The embodiment shown in FIGS. 2 and 4 also includes a flush port adaptor 90. The flush port adaptor 90 is generally tubular having a first end 91 removably securable over the intake port 26 of the valve housing 15 and a second end 92 of reduced diameter to which the first end 35 of the conduit 6 may be secured. A flush port 95 extends away from the flush port adaptor 90 and in flow communication therewith. The flush port 95 is generally positioned between the first end 91 and the second end 92 of the flush port adaptor. The flush port 95 includes sealing means such as seal 96 extending across the internal channel 97 thereof.

During use of the device 1, blood or fluids may dry in the valve causing the disk 30 to stick. The needle of a syringe containing a saline solution may be inserted through the seal 96 and into the flush port adaptor 90 such that a stream of saline solution may be directed toward the stuck disk 30 so as to loosen the disk thereby. When the needle is subsequently removed from the flush port 95 the seal 96 prevents air from being drawn back into the device 1 through the flush port 95.

For the purpose of this invention, the needle or catheter 61 and the chest tube 80 may commonly be referred to as pleural space entrance devices.

It is to be understood that while certain forms of the present invention have been illustrated and described herein, it is not to be limited to the specific forms or arrangement of parts described and shown.

What is claimed and desired to be secured by Letters Patent is as follows:

1. A pneumothorax treatment device comprising:
   (a) a one-way valve having a top end and a bottom end;
   (b) a suction port extending beyond said top end of said valve and in flow communication with said valve;
   (c) a conduit secured to and extending away from said bottom end of said valve in flow communication therewith;
   (d) receptacle means secured to said conduit for securing said pneumothorax treatment device to a pleural space entrance device such that said conduit is in flow communication with the pleural space entrance device;
   (e) flush port means for receiving a needle and directing a liquid stream from the needle toward said valve; said flush port means having self-sealing means for sealing said flush port means upon removal of a needle therefrom; said flush port means comprising a flush port extending from and in flow communication with said conduit and angled toward said valve.

2. A pneumothorax treatment device comprising:
   (a) a one-way valve having a top end and a bottom end;
   (b) a suction port extending beyond said top end of said valve and in flow communication with said valve;
   (c) a conduit secured to and extending away from said bottom end of said valve in flow communication therewith;
   (d) luer lock lug receptacle means secured to said conduit for threadingly receiving luer lock lugs on a pleural space entrance device incorporating luer lock lugs such that said conduit is in flow communication with the pleural space entrance device;
   (e) flush port means for receiving a needle and directing a liquid stream from the needle toward said valve; said flush port means having self-sealing means for sealing said flush port means upon removal of a needle therefrom; said flush port means comprising a flush port extending from and in flow communication with said conduit and angled toward said valve.

3. A pneumothorax treatment device comprising:
   (a) a one-way valve having a top end and a bottom end and a suction port extending beyond said top end; and
   (b) a conduit secured to and extending away from said bottom end of said one-way valve in flow communication therewith;
   (c) a luer lock lug receptacle including means for securing said receptacle in flow communication with a pleural space entrance device incorporating luer lock lugs;
   (d) a connection adapter including means for securing said connection adapter in flow communication with a chest tube; and
   (e) said conduit having means at a distal end thereof for interchangeably securing said luer lock lug receptacle and said connection adapter thereto in flow communication with said conduit.

4. The pneumothorax treatment device as disclosed in claim 3 further comprising:
   (f) flush port means for receiving a needle and directing a liquid stream from the needle toward said valve; said flush port means having self-sealing means for sealing said flush port means upon removal of a needle therefrom; said flush port means comprising a flush port extending from and in flow communication with said conduit and angled toward said valve.

* * * * *